US012562244B2

(12) United States Patent  (10) Patent No.: US 12,562,244 B2
Clarkson et al.  (45) Date of Patent: Feb. 24, 2026

(54) COMBINING DOMAIN-SPECIFIC ONTOLOGIES FOR LANGUAGE PROCESSING

(71) Applicant: INTERNATIONAL BUSINESS MACHINES CORPORATION, Armonk, NY (US)

(72) Inventors: Kenneth Lee Clarkson, Madison, NJ (US); Sanjana Sahayaraj, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 717 days.

(21) Appl. No.: 17/188,310

(22) Filed: Mar. 1, 2021

(65) Prior Publication Data

US 2022/0284996 A1   Sep. 8, 2022

(51) Int. Cl.
*G16H 10/60* (2018.01)
*G06F 40/284* (2020.01)
*G06F 40/30* (2020.01)

(52) U.S. Cl.
CPC ........... *G16H 10/60* (2018.01); *G06F 40/284* (2020.01); *G06F 40/30* (2020.01)

(58) Field of Classification Search
CPC ........ G06F 40/00; G06F 40/284; G06F 40/30; G06F 40/295
See application file for complete search history.

(56) References Cited

U.S. PATENT DOCUMENTS

| | | | |
|---|---|---|---|
| 7,630,981 B2 | 12/2009 | Xu et al. | |
| 8,135,730 B2 | 3/2012 | Lim et al. | |
| 10,025,774 B2 | 7/2018 | Coulet et al. | |
| 10,268,687 B1 | 4/2019 | McNair et al. | |
| 11,100,289 B1 * | 8/2021 | Kailasam | ................ G06F 40/30 |
| 2006/0053172 A1 | 3/2006 | Gardner et al. | |

(Continued)

FOREIGN PATENT DOCUMENTS

| | | |
|---|---|---|
| CN | 101777071 A | 7/2010 |
| CN | 103473222 A | 12/2013 |
| CN | 104679836 B | 6/2015 |

OTHER PUBLICATIONS

Charikar et al., "Finding frequent items in data streams.", 2004, Theoretical Computer Science, vol. 312 Issue 1, pp. 3-15 (Year: 2004).*

(Continued)

*Primary Examiner* — Hai Phan
*Assistant Examiner* — Alvin Iskender
(74) *Attorney, Agent, or Firm* — Tuamjian & Bitetto, P.C; Stosch Sabo

(57) ABSTRACT

Methods and systems for performing a natural language processing task include identifying hypernym/hyponym relations in a depth-wise ontology and identifying synonymy relations in a breadth-wise ontology. The depth-wise ontology and the breadth-wise ontology are combined into a combined ontology using the identified hypernym/hyponym relations and the identified synonymy relations. Enhanced hypernym/hyponym relations are embedded using the combined ontology. A natural language processing task is performed using the enhanced hypernym/hyponym relations and the combined ontology.

19 Claims, 7 Drawing Sheets

(56) References Cited

U.S. PATENT DOCUMENTS

| | | | |
|---|---|---|---|
| 2015/0347375 A1* | 12/2015 | Tremblay | G06F 16/367 |
| | | | 704/9 |
| 2017/0177703 A1* | 6/2017 | Liu | G06F 16/285 |
| 2019/0179845 A1 | 6/2019 | Romano | |
| 2021/0056168 A1* | 2/2021 | Bull | G06F 40/30 |

OTHER PUBLICATIONS

"Count sketch", Wikipedia (Year: 2023).*

Argerich et al., "Hash2Vec: Feature Hashing for Word Embeddings", 2016 (Year: 2016).*

Lambrix et al., "A unified approach for debugging is-a structure and mappings in networked taxonomies", 2013, J Biomed Semantics. https://www.ncbi.nlm.nih.gov/pmc/articles/PMC3851282 (Year: 2013).*

Maree et al, "Coupling semantic and statistical techniques for dynamically enriching web ontologies", 2013. https://arxiv.org/pdf/2004.11081 (Year: 2013).*

Nguyen et al., "Hierarchical Embeddings for Hypernymy Detection and Directionality", 2017. https://arxiv.org/abs/1707.07273 (Year: 2017).*

Liang et al. "Inferring Missing Links in Conceptual Taxonomies", 2017. IEEE. IEEE Transactions on Knowledge and Data Engineering, vol. 29 Issue 6, pp. 1281-1295 (Year: 2017).*

Nguyen et al., "Hierarchical Embeddings for Hypernymy Detection and Directionality", 2017 (Year: 2017).*

Larsen et al. "CountSketches, Feature Hashing and the Median of Three", Feb. 3, 2021 (Year: 2021).*

Lambrix et al. "A unified approach for debugging is-a structure and mappings in networked taxonomies", 2013 (Year: 2013).*

Maree et al, Mar. 2011, On the Merging of Domain-Specific Heterogenous Ontologies Using WordNet and Web-Pattern-Based Queries World Scientific Publishing, J. Inf. Knowl. Manag. vol. 10(1), pp. 23-36 (Year: 2011) (Year: 2011).*

Maree et al, Mar. 2011, On the Merging of Domain-Specific Heterogenous Ontologies Using WordNet and Web-Pattern-Based Queries World Scientific Publishing, J. Inf. Knowl. Manag. vol. 10(1), pp. 23-36 (Year: 2011).*

Saedi et al., "WordNet Embeddings", 2018, Association for Computational Linguistics, Proceedings of the 3rd Workshop on Representation Learning for NLP, pp. 122-131 (Year: 2018).*

Shi et al, "Higher-order Count Sketch: Dimensionality Reduction That Retains Efficient Tensor Operations", 2019 (Year: 2019).*

Brendan O'Connor, Mar. 13, 2012, "Cosine similarity, Pearson correlation, and OLS coefficients" (Year: 2012).*

Ivan Vulic, et al., "Specialising Word Vectors for Lexical Entailment", arXiv preprint arXiv:1710.06371. Oct. 17, 2017, pp. 1-12.

Ivan Vulic, et al., "Hyperlex: A Large-scale Evaluation of Graded Lexical Entailment", Computational Linguistics. Dec. 2017, pp. 1-50.

Haw-Shiuan Chang, et al., "Distributional Inclusion Vector Embedding for Unsupervised Hypernymy Detection", arXiv preprint arXiv:1710.00880. Oct. 2, 2017, pp. 1-20.

Adler Perotte, et al., "Diagnosis Code Assignment: Models and Evaluation Metrics", Journal of the American Medical Informatics Association. Mar. 1, 2014, pp. 231-237.

Maximilian Nickel, et al., "Poincaré Embeddings for Learning Hierarchical Representations", arXiv preprint arXiv:1705.08039. May 22, 2017, pp. 1-10.

Luu Anh Tuan, et al., "Learning Term Embeddings for Taxonomic Relation Identification Using DynamicWeighting Neural Network", InProceedings of the 2016 Conference on Empirical Methods in Natural Language Processing. Nov. 2016, pp. 403-413.

Matt Le, et al., "Inferring Concept Hierarchies from Text Corpora via Hyperbolic Embeddings", arXiv preprint arXiv:1902.00913. Feb. 3, 2019, pp. 1-11.

Qiuhao Lu, et al., "Learning Electronic Health Records through Hyperbolic Embedding of Medical Ontologies", InProceedings of the 10th ACM International Conference on Bioinformatics, Computational Biology and Health Informatics, Sep. 4, 2019, pp. 338-346.

Ben Athiwaratkun, et al., "Hierarchical Density Order Embeddings", arXiv preprint arXiv:1804.09843. Apr. 26, 2018,pp. 1-15.

Kim Anh Nguyen, et al., "Hierarchical Embeddings for Hypernymy Detection and Directionality", arXiv preprint arXiv:1707.07273. Jul. 23, 2017, pp. 1-11.

Kenneth L. Clarkson, et al., "Order Embeddings from Merged Ontologies using Sketching", arXiv preprint arXiv:2101.02158. Jan. 6, 2021, pp. 1-11.

Mell et al., "The NIST Definition of Cloud Computing", National Institute of Standards and Technology, Special Publication 800-145, Sep. 2011, pp. 1-7.

Charikar M. S. "Similarity estimation techniques from rounding algorithms," in Proceedings of the 34th Annual ACM Symposium on Theory of Computing, May 2002, pp. 380-388.

F. B. Rogers, "Medical subject headings," Bulletin of the Medical Library Association, pp. 114-116, Jan. 1963, vol. 51, No. 1.

G. A. Miller, "WordNet: An electronic lexical database", MIT Press, Oct. 1998, 8 pages.

Vendrov et al. "Order-embeddings of images and language," arXiv preprint, arXiv:1511.06361, Nov. 19, 2015, 13 pages.

Whetzel et al. "BioPortal: enhanced functionality via new web services from the National Center for Biomedical Ontology to access and use ontologies in software applications," Nucleic Acids Research, Jul. 2011, pp. W541-W545, vol. 39.

Wikipedia contributors, "Upper set," Wikipedia, the free encyclopedia [Online]. Available: https://en.wikipedia.org/wiki/Upper_set [Accessed: May 25, 2020], 1 page.

* cited by examiner

Embed hypernymy chains from distinct
ontologies
102

Combine ontologies with breadth and depth
104

Identify hypernymy relations in combined
ontology
106

Score combined ontology elements
108

Perform a natural language processing task
using the combined ontology
110

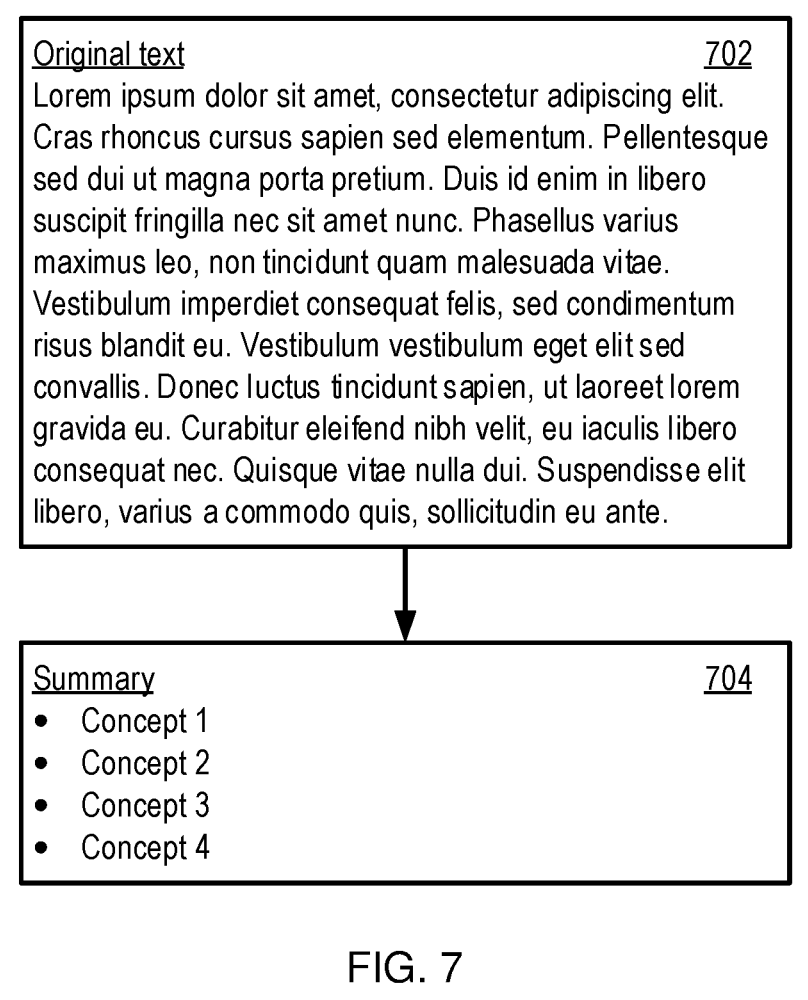

Original text                                         702
Lorem ipsum dolor sit amet, consectetur adipiscing elit.
Cras rhoncus cursus sapien sed elementum. Pellentesque
sed dui ut magna porta pretium. Duis id enim in libero
suscipit fringilla nec sit amet nunc. Phasellus varius
maximus leo, non tincidunt quam malesuada vitae.
Vestibulum imperdiet consequat felis, sed condimentum
risus blandit eu. Vestibulum vestibulum eget elit sed
convallis. Donec luctus tincidunt sapien, ut laoreet lorem
gravida eu. Curabitur eleifend nibh velit, eu iaculis libero
consequat nec. Quisque vitae nulla dui. Suspendisse elit
libero, varius a commodo quis, sollicitudin eu ante.

Summary                                               704
- Concept 1
- Concept 2
- Concept 3
- Concept 4

FIG. 7

COMBINING DOMAIN-SPECIFIC ONTOLOGIES FOR LANGUAGE PROCESSING

STATEMENT REGARDING PRIOR DISCLOSURES BY THE INVENTOR OR A JOINT INVENTOR

The following disclosure(s) are submitted under 35 U.S.C. § 102(b)(1)(A):

DISCLOSURE(S): Order Embeddings from Merged Ontologies using Sketching, by Kenneth L. Clarkson and Sanjana Sahayaraj, on Jan. 6, 2021.

BACKGROUND

The present invention generally relates to natural language processing, and, more particularly, to combinations of domain-specific ontologies that may be used to enhance natural language processing.

One challenge in natural language processing is to impart meaning to embedded natural language features, beyond the use of contextual information. For example, the medical field is an area where embedded feature representations are potentially interpretable.

Domain-specific information may be organized into ontologies, and may be derived from multiple different sources. Different ontologies may have overlapping, but non-identical, subject matter that pertains to a particular subject.

SUMMARY

A method for performing a natural language processing task include includes identifying hypernym/hyponym relations in a depth-wise ontology and identifying synonymy relations in a breadth-wise ontology. The depth-wise ontology and the breadth-wise ontology are combined into a combined ontology using the identified hypernym/hyponym relations and the identified synonymy relations. Enhanced hypernym/hyponym relations are embedded using the combined ontology. A natural language processing task is performed using the enhanced hypernym/hyponym relations and the combined ontology.

A system for performing a natural language processing task includes a hardware processor and a memory. The memory is configured to store computer program code that, when executed by the hardware processor, implements a relation embedder, an ontology combiner, and a natural language processing task. The relation embedder identifies hypernym/hyponym relations in a depth-wise ontology and synonymy relations in a breadth-wise ontology. The ontology combiner combines the depth-wise ontology and the breadth-wise ontology into a combined ontology using the identified hypernym/hyponym relations and the identified synonymy relations. The relation embedder further embeds enhanced hypernym/hyponym relations using the combined ontology. A natural language processing task uses the enhanced hypernym/hyponym relations and the combined ontology.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 7 is a diagram illustrating a text summarization natural language processing task, in accordance with an embodiment of the present invention.

DETAILED DESCRIPTION

Knowledge-rich feature representations may be created using ontologies. The knowledge and order information that is encoded in the ontologies may be extracted and then used for embedding. During subsequent natural language processing, this information can be leveraged to improve outcomes. For example, in medical fields, International Classification of Diseases (ICD) codes include rich information, including hierarchical classifications, that can be incorporated in embeddings to process electronic health record data.

Textual information from electronic health records, such as physician's notes for a patient, can be used to predict, for example, unplanned hospital re-admissions and in-hospital mortality prediction. Textual information may be represented as sequences of vectors corresponding to the sequence of words in the physician's notes. The more accurately the semantics of the words are represented by the vectors, the more accurate the predictions are likely to be. By capturing the relationships between different elements in an ontology, the quality of the embedded vectors is improved, resulting in an improvement in any language processing task that uses the vectors.

In the context of ontologies, the most effective embedding may not represent synonymy, but rather other relations between words. Other relations, such as lexical entailment, relationships between captions and images, "part-of" and "cause" relations, hypernym/hyponym, and other relations, may be captured in an ontology and may provide significant information regarding the underlying meaning of terms.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Figure 1:
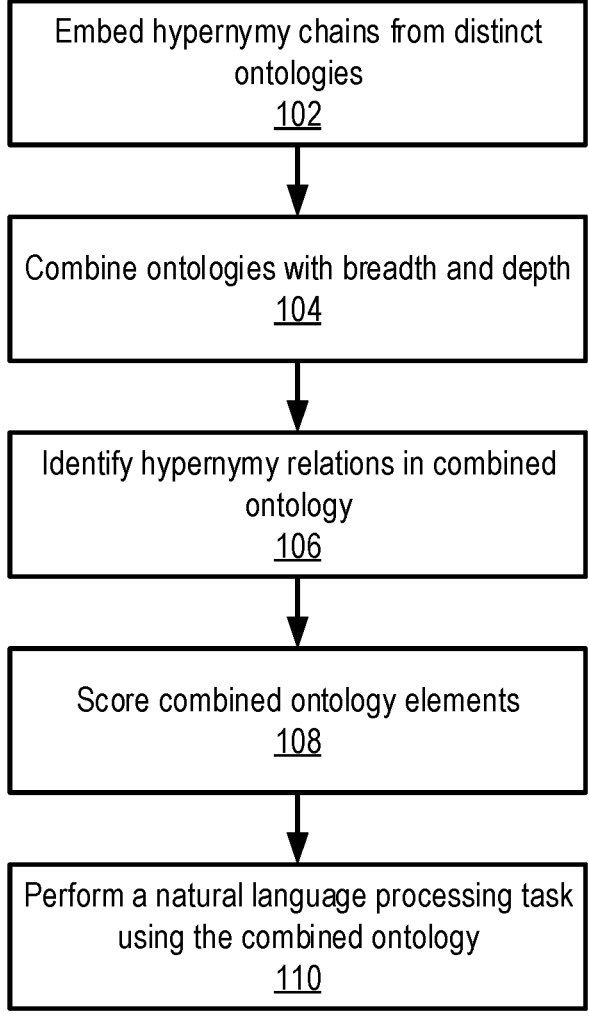
FIG. 1 is a block/flow diagram of a method of combining ontologies and embedding ontological relations for use in a natural language processing task, in accordance with an embodiment of the present invention.

Referring now to FIG. 1, a method for performing a natural language processing task using combined ontologies is shown. Hypernymy relationships, for example represented as embedded vectors, are used to identify correspondences between the distinct ontologies. In particular, block 102 considers each distinct ontology and represents the ordering relationships between terms. To capture this information, an approximate embedding may be determined, for terms with a partial order relation. For example, in the partially ordered set $(\mathcal{U}, \preceq)$, for all $x \in \mathcal{U}$, an upper set of x may be constructed as $\uparrow\{x\} \stackrel{\text{def}}{=} \{y | x \preceq y\}$. The characteristic vector $vec(x)_y \in \{0,1\}^{\mathcal{U}}$ of the upper set of x may be defined as:

$$vec(x)_y \in \{0, 1\} \stackrel{def}{=} \begin{cases} 1 & y \in \uparrow\{x\} \\ 0 & \text{otherwise} \end{cases}$$

A sketch vector $sk(vec(x)) \in \mathbb{R}^d$, for a target dimension, d, may be built so that, for $x, y \in \mathcal{U}$, the dot product $sk(vec(x)) \cdot sk(vec(y)) \approx vec(x) \cdot vec(y)$. The upper sets $\uparrow\{x\}$ represent the partial order via the subset relation, such that $x \preceq y \Leftrightarrow \uparrow\{x\} \supseteq \uparrow\{y\} \Leftrightarrow |\uparrow\{x\} \cap \uparrow\{y\}| = |\uparrow\{y\}|$. Since the characteristic vectors have the property that $vec(x) \cdot vec(y) = |\uparrow\{x\} \cap \uparrow\{y\}|$, then:

$$x \preceq y \Leftrightarrow vec(x) \cdot vec(y) = vec(y) \cdot vec(y)$$

Thus, vec(x) gives a direct representation of $(\mathcal{U}, \preceq)$ via the dot products. However, the vectors are in $\mathcal{U}$ dimensions, which may be too large to be useful. Thus, the sketching operation maps the vec(x) to lower-dimensional vectors, while approximately preserving the dot products.

In particular, two hash functions may be defined:

$$h_1 \colon \mathcal{U} \to [d]$$

$$h_2 \colon \mathcal{U} \to \{-1, +1\}$$

where $[d] \stackrel{\text{def}}{=} \{1, 2, \ldots, d\}$. In an ideal setting the hash functions are uniformly random over [d] and $\{-1, +1\}$, respectively, though in some embodiments, the second hash function may instead be implemented as the trivial $h_2 \colon \mathcal{U} \to \{+1\}$. Given a vector $v \in \{0,1\}^{\mathcal{U}}$, the sketch in $\mathbb{R}^d$ may have coordinates:

$$sk_c(v)_i \stackrel{def}{=} \sum_{y \colon h_1(y)=i} v_y h_2(y)$$

This may be expressed as the sum of the bit flips $h_2$ (y), over the $y \in \mathcal{U}$, such that $v_y = 1$ and y hashes to i, using $h_1$.

An embedding may be defined as, given $x \in \mathcal{U}$, the vector:

$$osk(x)_i \stackrel{def}{=} \sum_{\substack{x \leq y \\ h_1(y)=i}} h_2(y), \text{ for } i \in [d]$$

Assuming that $h_1$ and $h_2$ are random, then $sk_c(v) \cdot sk_c(w)$ is an unbiased estimator of $v \cdot w$, for v, $w \in \mathbb{R}^{\mathcal{U}}$ : $\mathbb{E}[sk_c(v) \cdot sk_c(w)] = v \cdot w$. Given sufficient randomness in the hash function outputs, any appropriate hash function may be used for $h_1$ and $h_2$. If v and w are very sparse, such that there are no collisions in their sketches, then $sk_c(v) \cdot sk_c(w) = v \cdot w$. This sparsity may be defined as $h_1(y) \neq h_1(y')$ for any y, y', with $v_y = v_{y'} = 1$ or $w_y = w_{y'} = 1$. More generally, the sparser that v and w are, the more accurate the sketch-based estimate of the dot product will be. The bit-flip hash function $h_2$ helps to reduce the effect of collisions, by averaging out their effects. However, with enough sparsity, $h_2$ may be omitted.

This embedding may be used to identify, for example, hypernym relations. This relation exists between specific word meanings, and identifies a "kind of" relation, for example where first concept is a "kind of" a second concept. One example is that the word "cat" represents a kind of "animal." In this example, the term "cat" is a hyponym of "animal," and "animal" is a hypernym of "cat." The upper sets $\uparrow\{x\}$ for each word meaning may be the set of all meanings that are direct or indirect hypernyms of it. Each group of meanings may be represented as the union of their respective upper sets. In some embodiments, these meanings may be represented as "synsets" in an ontology, referring to a set of one or more synonyms that are interchangeable in some context. Thus, union of synsets may be represented a union of the respective upper sets, which may be represented as "lemmas" in the ontology.

When a synset y is a hypernym of a union of synsets x, then $|\uparrow\{x\} \cap \uparrow\{y\}| = |\uparrow\{y\}|$ by construction. In this case, the ratio:

$$R_{x,y} \stackrel{def}{=} \frac{osk(x) \cdot osk(y)}{osk(y) \cdot osk(y)}$$

can be expected to be close to 1. If x and y are not related, then the ratio $R_{x,y} \approx 0$. Embedded representations can thus be tested using $R_{x,y}$, where the positive case may include all synsets y and all unions of synsets x that have one meaning (synset) that is a hyponym of y. When testing the accuracy of the representation, a proxy for the negative, unrelated case, may be found in choosing, for each synset y, a number of unions x at random. Classifications may be determined by comparison of $R_{x,y}$ to a threshold value.

While this represents one specific manner of embedding the partial order of terms in an ontology, it should be understood that other approaches may be used, such as simhash and minhash, but these approaches may be more complex and computationally expensive.

For this embedding to be useful in a particular domain, an ontology's elements may be organized as synsets and lemmas. In some cases, multiple domain-specific ontologies may be combined, composing related elements across the multiple ontologies. For example, using synonymous concepts of a first ontology as the lemmas of a synset, contextual and ordering information may be captured when matching concepts to another ontology.

Block 104 uses the embedded depth-wise ontology terms, which represent hypernym/hyponym relations, to combine two or more distinct ontologies, for example including a depth-wise ontology that tracks hypernym/hyponym relations and a breadth-wise ontology that tracks synonyms. Given a depth-wise ontology term, block 104 splits the term into a complex query with every word in the term. For example, in the specific context of a medical ontology, a given disease may be a term that is made up of multiple words, each contributing to the meaning of the term.

Block 104 queries a breadth-wise ontology to find a preferred label and synonyms for the main concept in the complex query, where the main concept may be defined in the ontology. For example, an ontology may include terms (T) that have several synonyms (S) linked with them. Thus, there may be a relationship indicated between T and S. However, there may be no relationship between the synonyms S for a given term T. In such an example, the term T may be a "main concept." Block 104 may then use heuristics, for example based on hypernym/hyponym or meronym relationships, to correlate terms across the ontologies using heuristics.

Block 106 then identifies hypernym/hyponym relations within the combined ontology. Hypernymy relations may be established by identifying members that take part in some sort of partial order, such as hypernymy or meronymy. The hypernymy relation can be identified heuristically. For example, a hypernym may be identified as a member having multiple synonyms, while the synonyms are not mutually synonymous. Thus, while "animal" may be identified as being synonymous with "cat," "dog," and "bird," these terms are not synonymous with one another, suggesting that the term "animal" is a hypernym to each. This heuristic may be applied, regardless of the type of partial order.

Block 108 scores the combined ontology and infers correlations. A function $R_{x,y}$ estimates relation strength between two elements to identify whether a hypernym relation exists between the two elements. For example, the function may output a value between 0 and 1, with values closer to 1 representing a hypernym/hyponym relation. Thus, whereas hypernym relations may be found heuristically in a first ontology, they may also be established in this manner in a parallel ontology that does not have hypernymy explicitly encoded.

Following the example of combining two parallel medical ontologies, some embodiments may score synonymy and hypernymy correlations differently. Most parts of deep hypernymy chains may be scored to a value that is close to 1, and a concept that is related between the two ontologies should have a value that is not close to 1. A main concept and its heuristically identified hyponyms may have a score value that is close to 1, while a main concept and its synonyms should have a value that is not close to 1.

In some embodiments, scoring mappings across ontologies may be used to discriminate between synonymy and hypernymy relations. A subset S of terms in a first ontology, and a subset M of terms in a second ontology, may be determined such that every term a in S has a synonym a' in M, and such that every term a' in M has a synonym a in S. There is an order on S, and an order on M, so that some measure of the correlation between a<b and a'<b' for any elements a and b. These mappings may be established through a scoring and can then be used to merge members or to perform other operations on ontologies.

Block 110 performs a natural language processing task using the combined ontologies and the ordered embeddings. For example, such combined ontologies may be particularly useful where ordered domain knowledge can be used, such as in summarization tasks and concept identification tasks. In the context of medical ontologies, this information can be used to identify disease mentions in electronic medical records, for example determining whether a disease is mentioned in a given sentence or paragraph. For example, as shown in FIG. 7, an original text 702 may be analyzed and a summary 704 may be generated that lists the concepts described in the original text 702.

Figure 2:
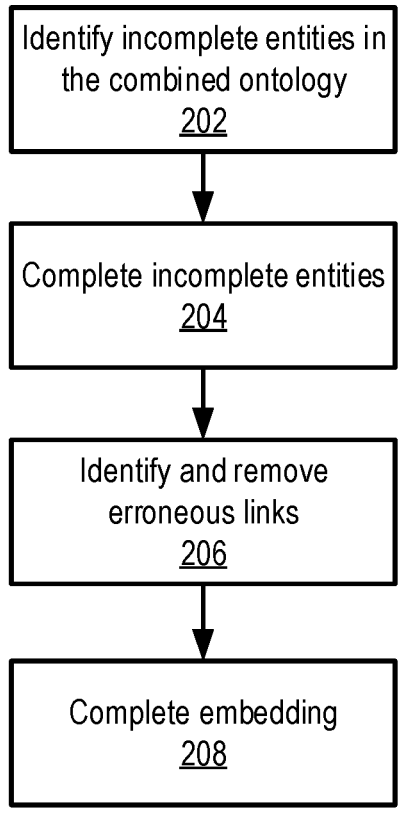
FIG. 2 is a block/flow diagram of a method of cleaning and improving a combined ontology, in accordance with an embodiment of the present invention.

Referring now to FIG. 2, a method for completing and correcting an ordered ontology is shown. Further processing can be performed on the combined ontology to improve its quality. For example, having verified and established a hypernym/hyponym relation or synonym relation between two entities in the combined ontology, a difference in properties between the two entities can be used to infer missing fields in members of the combined ontology. Field values of a first member, A, may be inferred from a provided field value of a second member, B, where A is a hyponym, hypernym, or synonym of B. The inference may involve clarifying importance and validation of properties to be included in a member that did not have them previously. The inference may include domain knowledge, or may be performed entirely automatically. Having established an order between two elements in an ontology, erroneous links may be identified, for example those that cause loops, and these links may be removed. By discovering these erroneous links while getting the embedded vectors, an additional step may be avoided, but the check may also be performed separately.

In block 202, a heuristic is applied that determines that a synonym or hyponym A of an entity B should have an equal or greater number of properties as compared to B. Thus, block 202 identifies entities in the combined ontology that are incomplete. This process may include, for example, identifying hypernymy relations from a first, depth-wise ontology, and establishing links with a second, breadth-wise ontology.

The synsets may be expanded using the breadth-wise ontology. Block 204 acts to complete the missing components, for example by filling in missing areas in the ontology, respecting hypernymy and synonymy relations. The hypernym/hyponym relations may be embedded, as described above.

Block 206 cleans the ontology by identifying erroneous links through fully connected components. This may include review by a human operator, to verify that the identified link is actually incorrect. Block 206 modifies the hypernym and hyponym set of the synset in question. This, in turn, modifies the strongly connected component and the ontology. With the corrected ontology in place, block 208 can complete the embedding of hypernym/hyponym relations.

Figure 3:
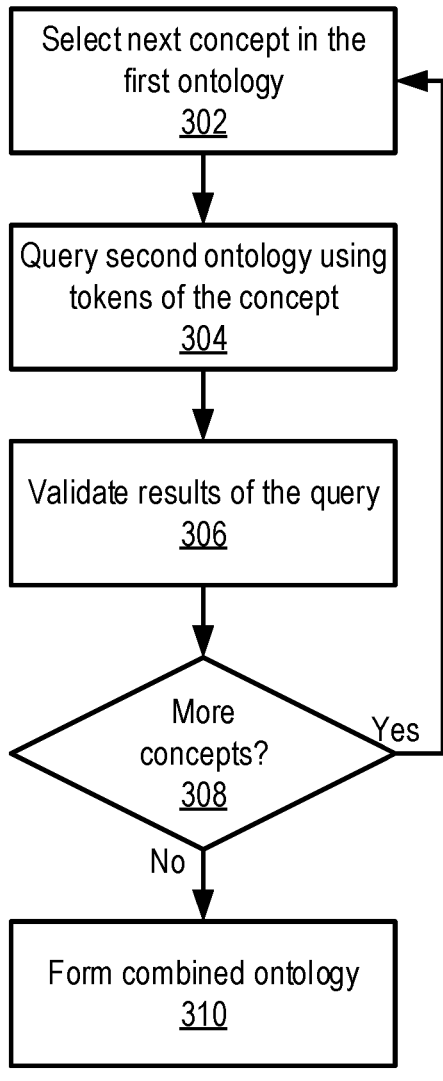
FIG. 3 is a block/flow diagram of a method of forming a combined ontology based on a depth-wise ontology and a breadth-wise ontology, in accordance with an embodiment of the present invention.

Referring now to FIG. 3, additional detail is shown for the combining of ontologies in block 104. Block 302 selects a first concept in the first ontology and block 304 executes a query on the second ontology that includes tokens of the concept. Out of the accepted return results from the second ontology, for example including prefLabel and synonym attributes, block 306 further validates the results, such that there is an overlap of at least one topic between the concept from the first ontology and the prefLabel, and between the concept and at least one synonym. This ensures sufficient contextual match between the entries of the first ontology and the second ontology, and also between the prefLabel information and the synonyms.

In one example, a concept from the first ontology, which may include phrase-like entries, may be, e.g., "Entire occipitomastoid suture of skull (body structure)." The second ontology may include more descriptive labels than the phrase-like entries of the first ontology. As a result, the results from the second ontology that pass the validation are likely to include information related to the concept and to exclude non-informative parts, like prepositions and determinants. Thus, a query on this concept may produce synonyms such as, "cranium," "skulls," "calvaria," "calvarium," with the associated prefLabel "skull." The query may also produce synonyms, on a different token, such as, "suture technique," "technique, suture," "technics, suture," with the associated prefLabel "suture techniques." In this manner, every token of the concept may be considered.

Block 308 then determines whether there are additional concepts in the first ontology that have not yet been considered. If so, processing returns to block 302 to select a next concept. If not, then block 310 determines the combined ontology on the basis of the validated query results. After having established the link between the first ontology and the second ontology through validation of query results, the data structures representing the ontology may be amended, to have it properly represent the combined ontology. For example, the synsets of a particular hypernym, which might have initially had only a few words, may increase to multiple synsets by borrowing corresponding synonymous/related concepts from the second ontology.

One effect of this combination is to help curate a relatively noisy ontology. For example, if the first ontology includes subject matter that is not related to the subject matter of the second ontology, those uninformative concepts will not be included, as there will be no related synonyms in the second ontology.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B)

only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), FPGAs, and/or PLAs.

These and other variations of a hardware processor subsystem are also contemplated in accordance with embodiments of the present invention.

Figure 4:
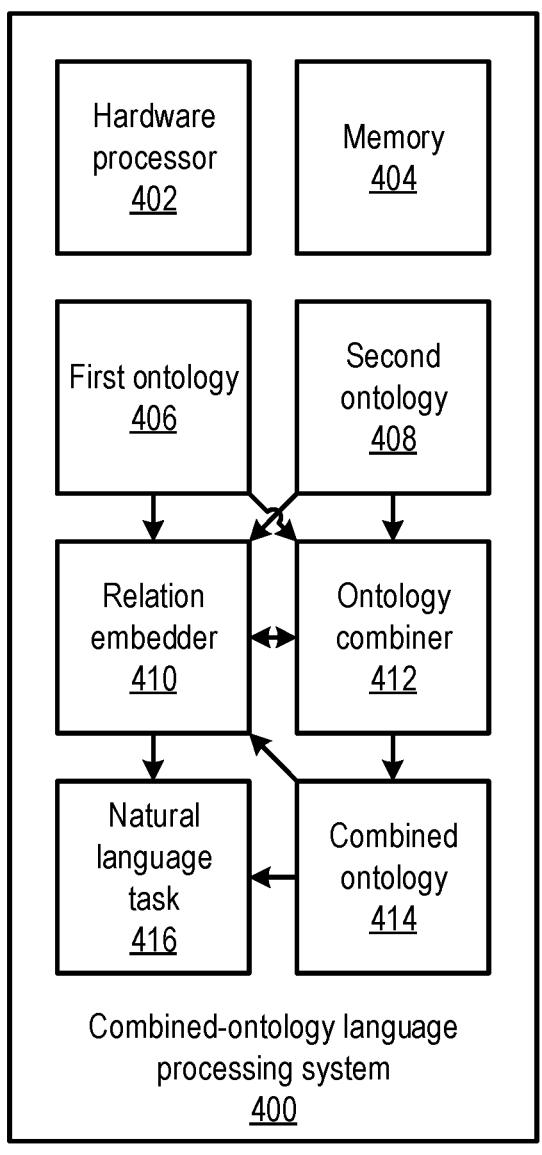
FIG. 4 is a block diagram of a language processing system that uses combined ontologies, in accordance with an embodiment of the present invention.

Referring now to FIG. 4, a combined-ontology language processing system 400 is shown. The system 400 includes a hardware processor 402 and a memory 404. The system 400 may include a variety of functional modules. Each such module may be implemented in any appropriate way. For example, such modules may be implemented as computer program code that is stored in the memory 404 and that is executed by the hardware processor to perform the described function. One or more modules may alternatively be implemented as one or more discrete hardware components, for example in the form of application-specific integrated chips or field-programmable gate arrays.

The memory 404 stores a first ontology 406 and a second ontology 408. These ontologies may be directed to shared subject matter, such as domain-specific medical information, and may be organized differently. For example, the first ontology 406 may be organized in a depth-wise fashion, with hypernym/hyponym relations being encoded, while the second ontology 408 may be organized in a breadth-wise fashion, with synonym relations being encoded. A relation embedder 410 works in with an ontology combiner 412 to produce a combined ontology 414 that uses the information from both ontologies to form an enriched knowledge base, with improved information relating to the relations between terms, and to produce improved embeddings of the relations between terms.

This improved embedded information may be used by a natural language task 416, providing superior results as compared to performance of the task using separate ontologies. For example, a summarization task that extracts the meaning of an electronic health record is improved by finding better representations for the relationships between terms, producing a more accurate summary of the content. In a medical concept identification task, for example, the ability to recognize whether a particular disease is mentioned in a given record is improved by better representing the relationships between terms. In one example, the task has an improved ability to recognize the mention of a particular disease that is described using non-standard terminology in medical records.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
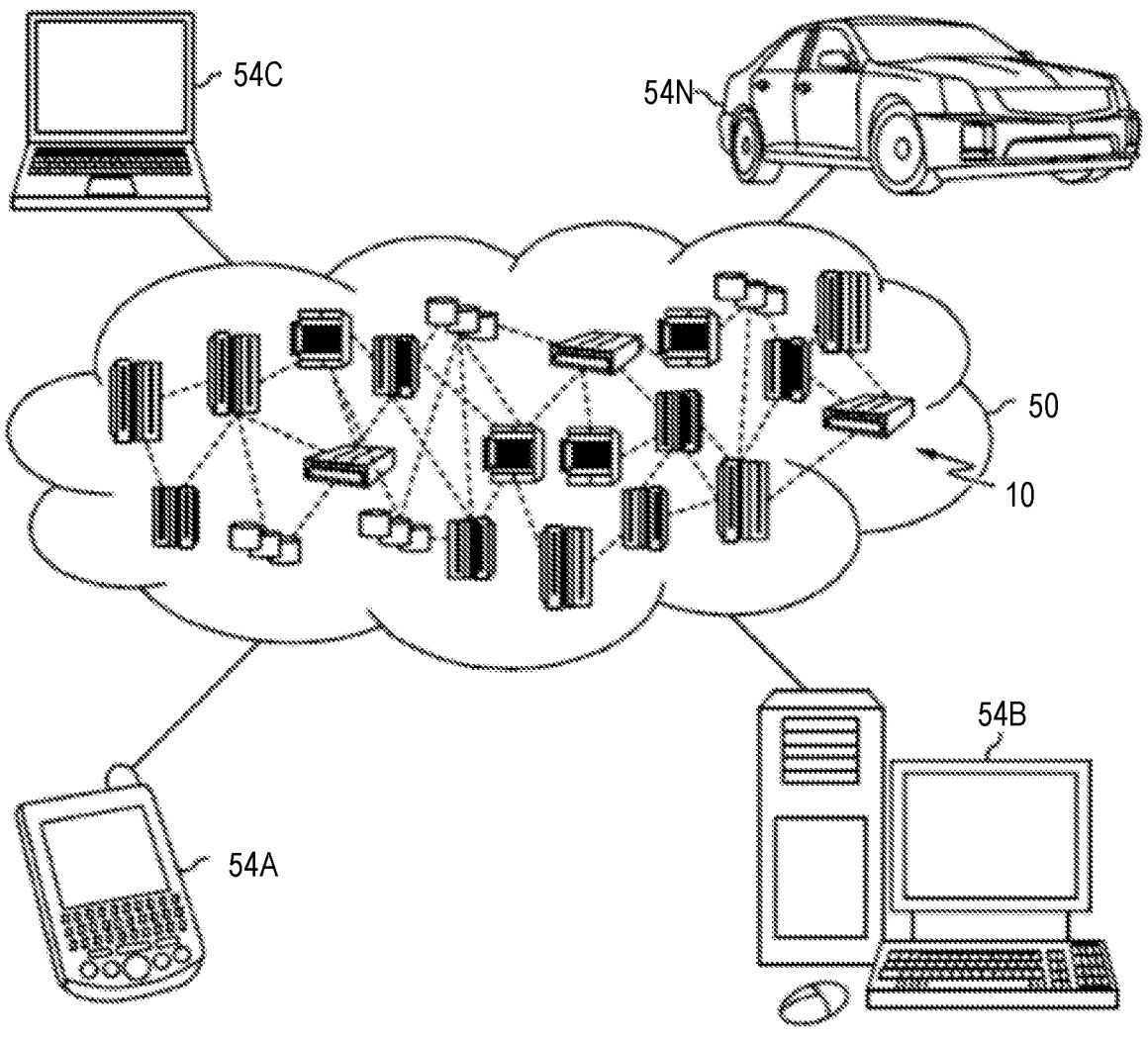
FIG. 5 is a block diagram showing an illustrative cloud computing environment having one or more cloud computing nodes with which local computing devices used by cloud consumers communicate in accordance with an embodiment of the present invention.

Referring now to FIG. 5, illustrative cloud computing environment 150 is depicted. As shown, cloud computing environment 150 includes one or more cloud computing nodes 110 with which local computing devices used by cloud consumers, such as, for example, personal digital assistant (PDA) or cellular telephone 154A, desktop computer 154B, laptop computer 154C, and/or automobile computer system 154N may communicate. Nodes 110 may communicate with one another. They may be grouped (not shown) physically or virtually, in one or more networks, such as Private, Community, Public, or Hybrid clouds as described hereinabove, or a combination thereof. This allows cloud computing environment 150 to offer infrastructure, platforms and/or software as services for which a cloud consumer does not need to maintain resources on a local computing device. It is understood that the types of computing devices 154A-N shown in FIG. 1 are intended to be illustrative only and that computing nodes 110 and cloud computing environment 150 can communicate with any type of computerized device over any type of network and/or network addressable connection (e.g., using a web browser).

Figure 6:
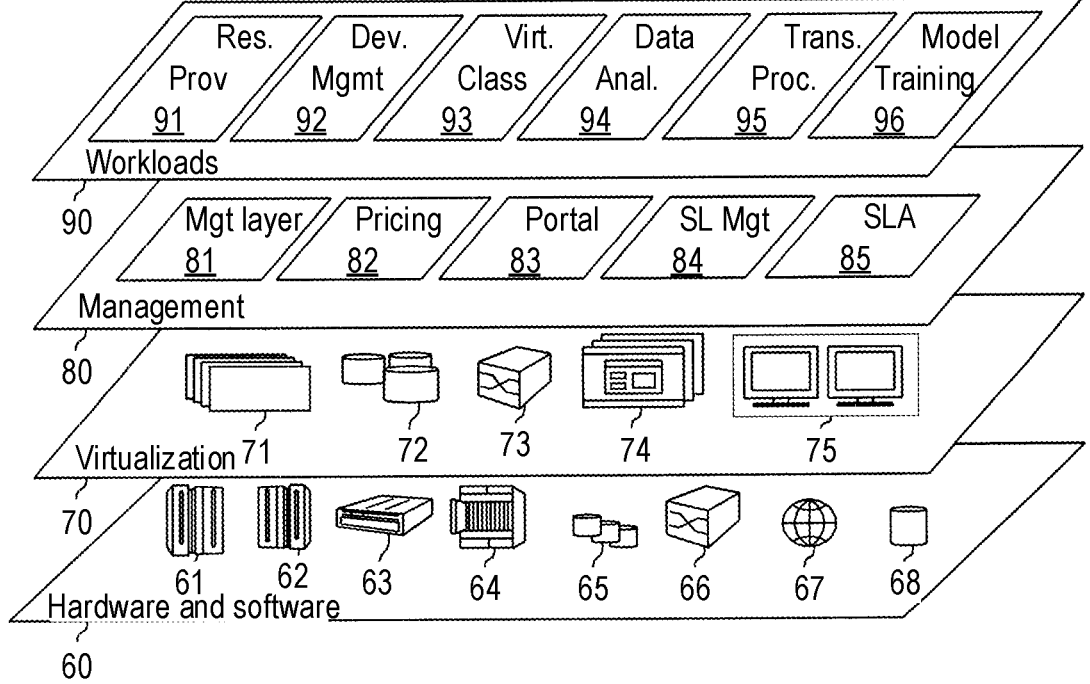
FIG. 6 is a block diagram showing a set of functional abstraction layers provided by a cloud computing environment in accordance with an embodiment of the present invention.

Referring now to FIG. 6, a set of functional abstraction layers provided by cloud computing environment 50 (FIG. 5) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and natural language processing 96.

Having described preferred embodiments of combining domain-specific ontologies for language processing (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A computer-implemented method for performing a natural language processing task, comprising:
   identifying hypernym/hyponym relations in a depth-wise ontology;
   identifying synonymy relations in a breadth-wise ontology;
   combining the depth-wise ontology and the breadth-wise ontology into a combined ontology using the identified hypernym/hyponym relations and the identified synonymy relations;
   identifying an incomplete entity in the combined ontology using a heuristic that includes determining that synonyms of the entity are not mutually synonymous;
   completing the incomplete entity to generate a corrected combined ontology;
   embedding a hypernym/hyponym relation of the corrected combined ontology after completing the incomplete entity using a sketch function that uses a first hash function, having a random output over d values, to generate a d-dimensional vector representation of a relationship between two terms based on the corrected combined ontology; and
   performing a natural language processing task using the new embedded hypernym/hyponym relation and the corrected combined ontology, including determining whether a first term and a second term are related according to a hypernym/hyponym relation by comparing a threshold to a ratio that is based on sketch function embeddings.

2. The method of claim 1, wherein identifying the hypernym/hyponym relations includes identifying a partial order between terms in the depth-wise ontology.

3. The method of claim 1, wherein the ratio is characterized as:

$$R_{x,y} = \frac{osk(x) \cdot osk(y)}{osk(y) \cdot osk(y)}$$

where y is a set of synonyms of the first term and x is a union of sets of synonyms of the second term and where osk(·) is the sketch function.

4. The method of claim 1, further comprising identifying and removing loops in the combined ontology by identifying hypernym/hyponym loops within the combined ontology.

5. The method of claim 1, wherein combining the depth-wise ontology and the breadth-wise ontology includes executing a query on the breadth-wise ontology using tokens from each concept in the depth-wise ontology.

6. The method of claim 5, further comprising validating results of the query from each concept in the depth-wise ontology to ensure a contextual match between the entries of the depth-wise ontology and the breadth-wise ontology.

7. The method of claim 1, wherein performing the natural language processing task includes a task selected from the group consisting of summarizing electronic health records and detecting concept mentions within electronic health records.

8. A non-transitory computer readable storage medium comprising a computer readable program for performing a natural language processing task, wherein the computer readable program when executed on a computer causes the computer to perform:
   identifying hypernym/hyponym relations in a depth-wise ontology;
   identifying synonymy relations in a breadth-wise ontology;
   combining the depth-wise ontology and the breadth-wise ontology into a combined ontology using the identified hypernym/hyponym relations and the identified synonymy relations;
   identifying an incomplete entity in the combined ontology using a heuristic that includes determining that synonyms of the entity are not mutually synonymous;
   completing the incomplete entity to generate a corrected combined ontology;
   embedding a hypernym/hyponym relation of the corrected combined ontology after completing the incomplete entity using a sketch function that uses a first hash function, having a random output over d values, to generate a d-dimensional vector representation of a relationship between two terms based on the corrected combined ontology; and
   performing a natural language processing task using the new embedded hypernym/hyponym relation and the corrected combined ontology, including determining whether a first term and a second term are related according to a hypernym/hyponym relation by comparing a threshold to a ratio that is based on sketch function embeddings.

9. A system for performing a natural language processing task, comprising:
   a hardware processor; and
   a memory, configured to store computer program code that, when executed by the hardware processor, implements:
      a relation embedder that identifies hypernym/hyponym relations in a depth-wise ontology and synonymy relations in a breadth-wise ontology;
      an ontology combiner that combines the depth-wise ontology and the breadth-wise ontology into a combined ontology using the identified hypernym/hyponym relations and the identified synonymy relations, that identifies an incomplete entity in the combined ontology using a heuristic that includes determining that synonyms of the entity are not mutually synonymous, that completes the incomplete entity to generate a corrected combined ontology, and that further embeds a hypernym/hyponym relation of the corrected combined ontology after completing the incomplete entity using a sketch function that uses a hash function, having a random output over d values, to generate a d-dimensional vector representation of a relationship between two terms based on the corrected combined ontology; and
      a natural language processing task that uses the new embedded hypernym/hyponym relation and the corrected combined ontology, including a determination of whether a first term and a second term are related according to a hypernym/hyponym relation by comparing a threshold to a ratio that is based on sketch function embeddings.

10. The system of claim 9, wherein the relation embedder identifies a partial order between terms in the depth-wise ontology.

11. The system of claim 9, wherein the ratio is characterized as:

$$R_{x,y} = \frac{osk(x) \cdot osk(y)}{osk(y) \cdot osk(y)}$$

where y is a set of synonyms of the first term and x is a union of sets of synonyms of the second term and where osk(·) is the sketch function.

12. The system of claim 9, wherein the ontology combiner further identifies and removes loops in the combined ontology by identifying hypernym/hyponym loops within the combined ontology.

13. The system of claim 9, wherein the ontology combiner executes a query on the breadth-wise ontology using tokens from each concept in the depth-wise ontology.

14. The system of claim 13, wherein the ontology combiner further validates results of the query from each concept in the depth-wise ontology to ensure a contextual match between the entries of the depth-wise ontology and the breadth-wise ontology.

15. The system of claim 9, wherein the natural language processing task includes a task selected from the group consisting of summarizing electronic health records and detecting concept mentions within electronic health records.

16. The method of claim 1, wherein the sketch function further uses a second hash function that encodes random bit flips to generate the d-dimensional vector representation.

17. The method of claim 16, wherein the hypernym/hyponym relations are represented as a vector in a partially ordered set, and wherein the sketch function sums the second hash function over vectors from the partially ordered set.

18. The method of claim 1, wherein the heuristic is that a synonym or hyponym of a first entity has an equal or greater number of entities than the first entity.

19. The system of claim 9, wherein the heuristic is that a synonym or hyponym of a first entity has an equal or greater number of entities than the first entity.

\* \* \* \* \*